United States Patent
Henshaw

(10) Patent No.: US 12,318,548 B2
(45) Date of Patent: Jun. 3, 2025

(54) MEDICAL DEVICE FOR USE IN A NERVE BLOCK PROCEDURE THAT OBVIATES THE NEED FOR INJECTING TEST DOSES AND A METHOD

(71) Applicant: Wake Forest University Health Sciences, Winston Salem, NC (US)

(72) Inventor: Daryl Henshaw, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 353 days.

(21) Appl. No.: 17/048,888

(22) PCT Filed: Apr. 19, 2019

(86) PCT No.: PCT/US2019/028328
§ 371 (c)(1),
(2) Date: Oct. 19, 2020

(87) PCT Pub. No.: WO2019/204732
PCT Pub. Date: Oct. 24, 2019

(65) Prior Publication Data
US 2021/0361905 A1  Nov. 25, 2021

Related U.S. Application Data

(60) Provisional application No. 62/660,016, filed on Apr. 19, 2018.

(51) Int. Cl.
*A61M 19/00* (2006.01)
*A61M 5/42* (2006.01)
*A61M 25/06* (2006.01)

(52) U.S. Cl.
CPC ............ *A61M 19/00* (2013.01); *A61M 5/427* (2013.01); *A61M 25/065* (2013.01)

(58) Field of Classification Search
CPC .... A61M 19/00; A61M 5/427; A61M 25/065; A61M 2021/0038; A61M 25/0026;
(Continued)

(56) References Cited

U.S. PATENT DOCUMENTS

| 4,675,004 A | 6/1987 | Hadford et al. |
| 6,068,623 A * | 5/2000 | Zadno-Azizi ......... A61M 25/10 600/585 |

(Continued)

OTHER PUBLICATIONS

International Search Report and Written Opinion dated Jul. 9, 2019 in copending PCT Application No. PCT/US2019/028328.

*Primary Examiner* — Chelsea E Stinson
*Assistant Examiner* — Hamza A Darb
(74) *Attorney, Agent, or Firm* — Thomas | Horstemeyer, LLP

(57) ABSTRACT

A medical device is provided for use in a nerve block procedure to dispense a numbing agent into a fascial plane of a patient's body that obviates the need for injecting a test dose to. The medical device can include a needle having a wire control mechanism and an echogenic feeler wire that can be viewed using an ultrasound probe. When the needle tip is positioned inside of the patient's body and the user controls the wire control mechanism to cause the feeler wire to move from the non-deployed state to the deployed state, a distal portion of the feeler wire extends out of the needle tip into the patient's body and moves within a region of the patient's body. Viewing the feeler wire on an ultrasound enables one to ascertain whether the needle tip is properly located in the fascial plane without having to inject a test dose.

20 Claims, 1 Drawing Sheet

(58) Field of Classification Search
CPC ............... A61M 5/158; A61M 5/1582; A61M 2005/1588; A61M 25/0067; A61M 25/0071; A61M 25/0082; A61M 25/06; A61M 2025/0166; A61M 2025/0175; A61M 2025/0177; A61M 37/0092; A61B 2017/3413; A61B 2090/3925; A61B 90/39

See application file for complete search history.

(56) References Cited

U.S. PATENT DOCUMENTS

| | | |
|---|---|---|
| 9,668,654 B2 | 6/2017 | Rajendran et al. |
| 2005/0020965 A1 | 1/2005 | Rioux et al. |
| 2006/0217655 A1 | 9/2006 | Vitullo et al. |
| 2007/0179508 A1 | 8/2007 | Arndt |
| 2011/0082370 A1* | 4/2011 | Ducharme ....... A61B 17/00234 600/249 |
| 2014/0073926 A1* | 3/2014 | Rajendran ............. A61B 8/481 600/478 |
| 2014/0275992 A1* | 9/2014 | Choi ................. A61B 17/1671 600/424 |

* cited by examiner

MEDICAL DEVICE FOR USE IN A NERVE BLOCK PROCEDURE THAT OBVIATES THE NEED FOR INJECTING TEST DOSES AND A METHOD

CROSS-REFERENCE TO RELATED APPLICATIONS

The present application is a U.S. National Phase filing under 35 U.S.C. § 371 of PCT International Application No. PCT/US2019/028328 filed on Apr. 19, 2019, that claims the benefit of and priority to the filing date of U.S. provisional application entitled "A MEDICAL DEVICE FOR USE IN A NERVE BLOCK PROCEDURE THAT OBVIATES THE NEED FOR INJECTING TEST DOSES, AND A METHOD" having Ser. No. 62/660,016, filed Apr. 19, 2018, the contents of which are incorporated by reference herein in their entireties.

TECHNICAL FIELD

The present disclosure generally relates to medical devices, and more particularly, to a medical device for use in nerve blocking procedures that obviates the need to inject a test dose.

BACKGROUND

Some types of peripheral nerve blocks aim to deliver local anesthetic to a specific fascial plane. The needles currently used have been relatively unchanged throughout the history of their use and consist of a hollow bore needle to allow for the injection of the local anesthetic medications. The anesthetic will subsequently spread to bathe the various small sensory nerves that transverse the plane. Ultrasound is used to guide the needle between the layers of fascia. Once a clinician believes that the needle tip is properly located, a small volume of local anesthetic or saline (fluid) is injected as a "test dose" to see if the fluid spreads in the correct plane. If it does, then the remainder of the injection is completed. If the "test dose" is injected and is not felt to be visualized in the preferred location (which is common), the practitioner then adjusts the needle tip location and repeats the process. Unfortunately, the injection of fluid, even in small doses, distorts the tissue planes and the ultrasound image, making it more difficult with each "test dose" to maintain a good image with the ultrasound and successfully complete the procedure.

Accordingly, a need exists for an alternate method for identifying the correct tissue plane without the need to perform test dose injections. Removing the need for a test dose preserves the ultrasound image, potentially increasing the success rate of the procedure.

SUMMARY

In various aspects, medical devices are provided that overcome one or more of the aforementioned problems. For example, a medical device is provided for use in a nerve block procedure to dispense a numbing agent into a fascial plane of a patient's body that obviates the need for injecting a test dose to determine whether the needle tip is properly located.

In some aspects, the medical device includes a needle having a proximal end, a distal end and at least a first hollow bore extending from the proximal end to the distal end; a wire control mechanism; and a feeler wire extending through the first hollow bore of the needle, the feeler wire having a proximal end and a distal end, the feeler wire comprising an echogenic material that is reflective to ultrasound energy, the proximal end of the feeler wire being mechanically coupled to the wire control mechanism, wherein the wire control mechanism is configured to be controlled by a user to move the feeler wire from a non-deployed state to a deployed state, and vice versa, wherein when the distal end of the needle is positioned inside of the patient's body and the user controls the wire control mechanism to cause the feeler wire to move from the non-deployed state to the deployed state, a distal portion of the feeler wire that includes the distal end of the feeler wire extends out of the distal end of the needle into the patient's body and moves within a region of the patient's body.

The feeler wire can have a degree of stiffness that ensures that the feeler wire maintains an elongated shape when the feeler wire is traveling within the fascial plane, the feeler wire having a degree of flexibility that ensures that the elongated shape of the feeler wire temporarily deforms if the distal portion of the feeler wire contacts tissue outside of the fascial plane, wherein the temporary deformation of the elongated shape is observable by the ultrasound machine.

In some aspects, a medical device is provided for use in a nerve block procedure to dispense a numbing agent into a fascial plane of a patient's body, the medical device having: a needle having a proximal end, a distal end and at least a first hollow bore extending from the proximal end to the distal end; a wire control mechanism; and a feeler wire extending through the first hollow bore of the needle, the feeler wire comprising an echogenic material that is reflective to ultrasound energy, the feeler wire having a proximal end and a distal end and, the proximal end of the feeler wire being mechanically coupled to the wire control mechanism, wherein the wire control mechanism is configured to be controlled by the user to move the feeler wire from a non-deployed state to a deployed state, and vice versa, wherein when the distal end of the needle is disposed inside of the patient's body and the user controls the wire control mechanism to cause the feeler wire to move from the non-deployed state to the deployed state, a distal portion of the feeler wire that includes the distal end of the feeler wire extends out of the distal end of the needle into the patient's body and moves within a region of the patient's body, wherein the feeler wire has a degree of stiffness that ensures that the feeler wire maintains an elongated shape when the feeler wire is moving within the fascial plane, the feeler wire having a degree of flexibility that ensures that the elongated shape of the feeler wire temporarily deforms if the distal portion of the feeler wire contacts tissue outside of the fascial plane, wherein the temporary deformation of the elongated shape is observable by an ultrasound machine.

Methods of using the devices, e.g. for dispensing a nerve block agent into the facial plane, are also provided. In some aspects, a method for locating a fascial plane when performing a nerve block procedure is provided, the method including: inserting a distal end of a needle into a region of a patient's body, the needle having a proximal end and at least a first hollow bore extending from the proximal end to the distal end; using a wire control mechanism to control movement of a feeler wire that extends through the first hollow bore of the needle, the feeler wire having a proximal end and a distal end and comprising an echogenic material that is reflective to ultrasound energy, the proximal end of the feeler wire being mechanically coupled to the wire control mechanism, wherein the feeler wire is controllable via the wire control mechanism to move the feeler wire from a non-deployed state to a deployed state, and vice versa, wherein when the distal end of the needle is disposed inside of the region of the patient's body and the feeler wire is moved from the non-deployed state to the deployed state, a distal portion of the feeler wire that includes the distal end of the feeler wire extends out of the distal end of the needle into the patient's body and moves within the region of the patient's body; and with an ultrasound machine, determining whether the distal portion of the feeler wire is within the fascial plane based at least on a shape of the distal portion of the feeler wire.

Other systems, methods, features, and advantages of medical devices and methods will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
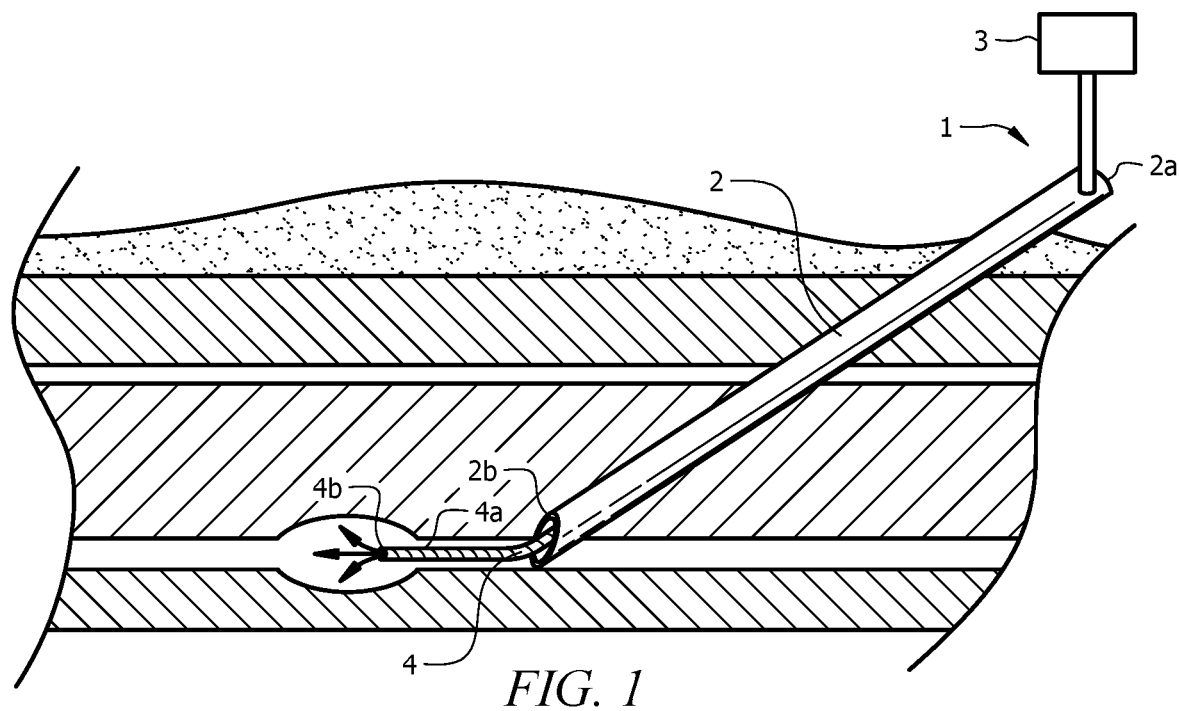
FIG. 1 is a side perspective view of a first exemplary medical device in accordance with the various aspects of the disclosure.

In accordance with the inventive principles and concepts described herein, a medical device is provided for use in a nerve block procedure to dispense a numbing agent into a fascial plane of a patient's body that obviates the need for injecting a test dose to determine whether the needle tip is properly located.

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Aspects and features of the present disclosure will employ, unless otherwise indicated, medical and surgical techniques, as well as techniques for the design and manufacture of medical devices and surgical tools and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some aspects, the term "about" can include traditional rounding according to significant figures of the numerical value. In addition, the phrase "about 'x' to 'y'", where 'x' and 'y' are numerical values, includes "about 'x' to about 'y'".

In some instances, units may be used herein that are non-metric or non-SI units. Such units may be, for instance, in U.S. Customary Measures, e.g., as set forth by the National Institute of Standards and Technology, Department of Commerce, United States of America in publications such as NIST HB 44, NIST HB 133, NIST SP 811, NIST SP 1038, NBS Miscellaneous Publication 214, and the like. The units in U.S. Customary Measures are understood to include equivalent dimensions in metric and other units (e.g., a dimension disclosed as "1 inch" is intended to mean an equivalent dimension of "2.5 cm"; a unit disclosed as "1 pcf" is intended to mean an equivalent dimension of 0.157 kN/m$^3$; or a unit disclosed 100° F. is intended to mean an equivalent dimension of 37.8° C.; and the like) as understood by a person of ordinary skill in the art.

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in aspects of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The medical device can include a needle, a wire control mechanism and a feeler wire. The feeler wire is made of or otherwise includes an echogenic material to enable to it to be viewed using an ultrasound probe. The feeler wire extends through a hollow bore of the needle. A proximal end of the feeler wire is mechanically coupled to the wire control mechanism, which is configured to be controlled by a user to move the feeler wire from a non-deployed state to a deployed state, and vice versa. When the needle tip is positioned inside of the patient's body and the user controls the wire control mechanism to cause the feeler wire to move from the non-deployed state to the deployed state, a distal portion of the feeler wire that includes the distal end of the feeler wire extends out of the distal end of the needle into the patient's body and moves within a region of the patient's body. By viewing the feeler wire on an ultrasound device, the user is able to ascertain whether the needle tip is properly located in the fascial plane without having to inject a test dose.

FIG. 1 is a side perspective view of the first exemplary medical device 1 in accordance with the various aspects of the disclosure. A needle 2 of the medical device has a proximal end 2a, a distal end 2b, which is the needle tip, and at least a first hollow bore extending from the proximal end 2a to the distal end 2b. A wire control mechanism 3 of the medical device 1 is mechanically coupled to a proximal end of a feeler wire 4 of the medical device 1. The feeler wire 4 extends through the first hollow bore of the needle 2 and includes an echogenic material that is reflective to ultrasound energy.

The wire control mechanism 3 is configured to be controlled by a user to move the feeler wire 4 from a non-deployed state to a deployed state, and vice versa. When the distal end 2b of the needle 2, i.e., the needle tip, is positioned inside of the patient's body, the user controls the wire control mechanism 3 to cause the feeler wire 4 to move from the non-deployed state to the deployed state. In the deployed state, a distal portion 4a of the feeler wire 4 that includes the distal end 4b of the feeler wire 4 extends out of the distal end 2b of the needle 2 into the patient's body and moves within a region of the patient's body. Because the feeler wire 4 is viewable on the ultrasound device, the user is able to determine whether or not the feeler wire 4 has located the fascial plane without having to inject a test dose. If the user determines that the feeler wire 4 is not located in the fascial plane, the user operates the wire control mechanism 3 to move the feeler wire 4 from the deployed state to the non-deployed state. The user then partially or fully withdraws the needle tip 2b from the patient and reinserts it at a different location in the patient's body. The user then operates the wire control mechanism 3 to redeploy the feeler wire 4 and determines, based on the ultrasound image, whether the feeler wire 4 is now located in the fascial plane. This process can continue until the user has positioned the feeler wire 4 in the fascial plane. Once the feeler wire 4 is properly located in the fascial plane, nerve block fluid is injected into the fascial plane through either the distal end 4b of the feeler wire 4 or through the needle tip 2b.

In various aspects, the feeler wire 4 has a degree of stiffness that ensures that the feeler wire 4 maintains an elongated shape when the feeler wire is traveling within the fascial plane, and has a degree of flexibility that ensures that the elongated shape of the feeler wire 4 temporarily deforms if the distal portion 4a of the feeler wire 4 contacts tissue outside of the fascial plane. The temporary deformation of the elongated shape is observable with the ultrasound device, and therefore the user can easily determine whether the distal end 4b of the feeler wire 4 is currently located in the fascial plane.

In some aspects, the needle 2 has a gauge that ranges between about 21 and 25, although design is not limited to the needle 2 having any particular dimensions, as will be understood by those of skill in the art. In accordance with some aspects, the feeler wire 4 comprises Nitinol, although any materials having suitable properties may be used for the feeler wire 4.

In accordance some aspects, the feeler wire 4 has a hollow bore. Once the feeler wire 4 is properly located in the fascial plane, as determined based on the ultrasound image, nerve block fluid is injected through the hollow bore of the feeler wire 4 and out of the distal end 4b of the feeler wire 4 into the fascial plane.

Figure 2:
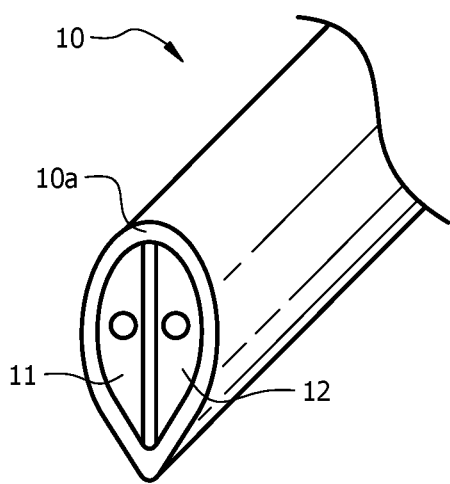
FIG. 2 is an end perspective view of the first exemplary medical device in accordance with the various aspects of the disclosure.

FIG. 2 is an end perspective view of the medical device 10 in accordance with another embodiment. The wire control mechanism used with the medical device 10 may be identical to the wire control mechanism 3 shown in FIG. 1. Like the medical device 1 shown in FIG. 1, the medical device 10 shown in FIG. 2 has a feeler wire (not shown) that is controlled by the wire control mechanism 3. However, the medical device 10 has first and second hollow bores, 11 and 12, respectively. The feeler wire travels along the first hollow bore 11 and the nerve block fluid travels along the second hollow bore 12. Therefore, in this embodiment, the nerve block fluid is dispensed through the needle tip 10a rather than through the distal end of the feeler wire. In this embodiment, it is not necessary for the feeler wire to have a hollow bore.

In accordance with some aspects, a catheter (not shown) extends over and about the feeler wire. A catheter can extend through and within the feeler wire. In accordance with various aspects, a catheter is disposed within the second hollow bore 12 of the needle to allow the catheter to extend through the second hollow bore 12 and through the needle tip into the region of the patient's body.

It should be noted that the device has been described with respect to illustrative embodiments for the purpose of describing the principles and concepts of the disclosure. The dis closure is not limited to these aspects. For example, while the device has been described with reference to particular configurations of the medical devices 1 and 10, the medical devices 1 and 10 may have any suitable configuration. Also, while the inventive principles and concepts have been described with reference to performing a nerve block procedure, the medical device may be used for any purpose for which it is suited. As will be understood by those skilled in the art in view of the description being provided herein, many modifications may be made to the embodiments described herein while still achieving the goals of the invention, and all such modifications are within the scope of the invention.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The disclosure will be better understood upon viewing the following aspects which should not be confused with the claims. Each of the aspects described below can, in some instances, be combined with other numbered aspects below, with other aspects descried herein, or a combination thereof.

Aspect 1. A medical device for use in a nerve block procedure to dispense a numbing agent into a fascial plane of a patient's body, the medical device including: a needle having a proximal end, a distal end and at least a first hollow bore extending from the proximal end to the distal end; a wire control mechanism; and a feeler wire extending through the first hollow bore of the needle, the feeler wire having a proximal end and a distal end, the feeler wire comprising an echogenic material that is reflective to ultrasound energy, the proximal end of the feeler wire being mechanically coupled to the wire control mechanism, wherein the wire control mechanism is configured to be controlled by a user to move the feeler wire from a non-deployed state to a deployed state, and vice versa, wherein when the distal end of the needle is positioned inside of the patient's body and the user controls the wire control mechanism to cause the feeler wire to move from the non-deployed state to the deployed state, a distal portion of the feeler wire that includes the distal end of the feeler wire extends out of the distal end of the needle into the patient's body and moves within a region of the patient's body.

Aspect 2. The medical device of any one of Aspects 1-15, wherein the movement of the distal portion within the region and a shape of the distal portion within the region is observable by an ultrasound machine to determine whether or not the distal portion of the feeler wire is within the fascial plane.

Aspect 3. The medical device of any one of Aspects 1-15, wherein the feeler wire has a degree of stiffness that ensures that the feeler wire maintains an elongated shape when the feeler wire is traveling within the fascial plane, the feeler wire having a degree of flexibility that ensures that the elongated shape of the feeler wire temporarily deforms if the distal portion of the feeler wire contacts tissue outside of the fascial plane, wherein the temporary deformation of the elongated shape is observable by the ultrasound machine.

Aspect 4. The medical device of any one of Aspects 1-15, wherein the needle has a gauge that ranges between about 21 and 25.

Aspect 5. The medical device of any one of Aspects 1-15, wherein the feeler wire comprises Nitinol.

Aspect 6. The medical device of any one of Aspects 1-15, wherein the feeler wire has a hollow bore.

Aspect 7. The medical device of any one of Aspects 1-15, wherein the hollow bore of the feeler wire is adapted to allow a fluid to be passed through the hollow bore of the feeler wire and through the distal end of the feeler wire into the region of the patient's body.

Aspect 8. The medical device of any one of Aspects 1-15, further comprising: a catheter that extends over and about the feeler wire.

Aspect 9. The medical device of any one of Aspects 1-15, further comprising: a catheter that extends through and within the feeler wire.

Aspect 10. The medical device of any one of Aspects 1-15, wherein the needle has at least a second hollow bore extending from the proximal end of the needle to the distal end of the needle generally parallel to the first hollow bore.

Aspect 11. The medical device of any one of Aspects 1-15, wherein the second hollow bore of the needle is adapted to allow a fluid to be passed through the second hollow bore of the needle and to be injected into the region of the patient's body through the distal end of the needle.

Aspect 12. The medical device of any one of Aspects 1-15, wherein the needle has a gauge that ranges between about 21 and 25.

Aspect 13. The medical device of any one of Aspects 1-15, wherein the feeler wire comprises Nitinol.

Aspect 14. The medical device of any one of Aspects 1-15, further comprising: a catheter disposed within the second hollow bore, wherein the second hollow bore of the needle is adapted to allow the catheter to extend through the second hollow bore of the needle and through the distal end of the needle into the region of the patient's body.

Aspect 15. A medical device for use in a nerve block procedure to dispense a numbing agent into a fascial plane of a patient's body, the medical device comprising: a needle having a proximal end, a distal end and at least a first hollow bore extending from the proximal end to the distal end; a wire control mechanism; and a feeler wire extending through the first hollow bore of the needle, the feeler wire comprising an echogenic material that is reflective to ultrasound energy, the feeler wire having a proximal end and a distal end and, the proximal end of the feeler wire being mechanically coupled to the wire control mechanism, wherein the wire control mechanism is configured to be controlled by the user to move the feeler wire from a non-deployed state to a deployed state, and vice versa, wherein when the distal end of the needle is disposed inside of the patient's body and the user controls the wire control mechanism to cause the feeler wire to move from the non-deployed state to the deployed state, a distal portion of the feeler wire that includes the distal end of the feeler wire extends out of the distal end of the needle into the patient's body and moves within a region of the patient's body, wherein the feeler wire has a degree of stiffness that ensures that the feeler wire maintains an elongated shape when the feeler wire is moving within the fascial plane, the feeler wire having a degree of flexibility that ensures that the elongated shape of the feeler wire temporarily deforms if the distal portion of the feeler wire contacts tissue outside of the fascial plane, wherein the temporary deformation of the elongated shape is observable by an ultrasound machine.

Aspect 16. A method for locating a fascial plane when performing a nerve block procedure, the method comprising: inserting a distal end of a needle into a region of a patient's body, the needle having a proximal end and at least a first hollow bore extending from the proximal end to the distal end; using a wire control mechanism to control movement of a feeler wire that extends through the first hollow bore of the needle, the feeler wire having a proximal end and a distal end and comprising an echogenic material that is reflective to ultrasound energy, the proximal end of the feeler wire being mechanically coupled to the wire control mechanism, wherein the feeler wire is controllable via the wire control mechanism to move the feeler wire from a non-deployed state to a deployed state, and vice versa, wherein when the distal end of the needle is disposed inside of the region of the patient's body and the feeler wire is moved from the non-deployed state to the deployed state, a distal portion of the feeler wire that includes the distal end of the feeler wire extends out of the distal end of the needle into the patient's body and moves within the region of the patient's body; and with an ultrasound machine, determining whether the distal portion of the feeler wire is within the fascial plane based at least on a shape of the distal portion of the feeler wire.

Aspect 17. The method of any one of Aspects 16-21, wherein the feeler wire has a degree of stiffness that ensures that the feeler wire maintains an elongated shape when the feeler wire is moving within the fascial plane, the feeler wire having a degree of flexibility that ensures that the elongated shape of the feeler wire temporarily deforms if the distal portion of the feeler wire contacts tissue outside of the fascial plane, wherein the temporary deformation of the elongated shape is observable by the ultrasound machine.

Aspect 18. The method of any one of Aspects 16-21, wherein the feeler wire has a hollow bore to allow a fluid to be passed through the hollow bore of the feeler wire and to be injected into the region of the patient's body through the distal end of the feeler wire, the method further comprising: if a determination is made that the distal portion of the feeler wire is within the fascial plane, injecting fluid through the hollow bore of the feeler wire and through the distal end of the feeler wire into the region of the patient's body.

Aspect 19. The method of any one of Aspects 16-21, wherein the needle has a second hollow bore extending from the proximal end of the needle to the distal end of the needle generally parallel to the first hollow bore of the needle, wherein the second hollow bore of the needle is adapted to allow a fluid to be passed through the second hollow bore of the needle and to be injected into the region of the patient's body through the distal end of the needle, the method further comprising: if a determination is made that the distal portion of the feeler wire is within the fascial plane, injecting fluid through the second hollow bore of the needle and through the distal end of the needle into the region of the patient's body.

Aspect 20. The method of any one of Aspects 16-21, further comprising: if a determination is made that the distal portion of the feeler wire is not within the fascial plane, with the wire control mechanism, moving the feeler wire from the deployed state to the non-deployed state; repositioning the needle by inserting the distal end of the needle into a new region of a patient's body; with the wire control mechanism, moving the feeler wire from the non-deployed state to the deployed state to cause the distal portion of the feeler wire to extend out of the distal end of the needle into the patient's body and move within the new region of the patient's body; and with the ultrasound machine, determining whether the distal portion of the feeler wire is within the fascial plane based at least on the shape of the distal portion of the feeler wire.

Aspect 21. The method of any one of Aspects 16-20, wherein the method is performed with a device according to any one of claims 1-15.

I claim:

1. A medical device for use in a nerve block procedure to dispense a numbing agent into a fascial plane of a patient's body, the medical device comprising:
   a needle having a proximal end, a distal end, a first hollow bore extending from the proximal end to the distal end, and a second hollow bore extending from the proximal end to the distal end, wherein the distal end of the needle is formed by the first hollow bore and the second hollow bore coming together in a sharpened bevel to allow for permeation of the patient's body for the needle to reach the fascial plane;
   a wire control mechanism; and
   a feeler wire extending through the first hollow bore of the needle, the feeler wire having a proximal end and a distal end, the feeler wire comprising an echogenic material that is reflective to ultrasound energy, the proximal end of the feeler wire being mechanically coupled to the wire control mechanism, wherein the wire control mechanism is configured to be controlled by a user to move the feeler wire from a non-deployed state to a deployed state, and vice versa, wherein when the distal end of the needle is positioned inside of the patient's body and the user controls the wire control mechanism to cause the feeler wire to move from the non-deployed state to the deployed state, a distal portion of the feeler wire that includes the distal end of the feeler wire extends out of the distal end of the needle into the patient's body and moves within a region of the fascial plane of the patient's body, wherein the feeler wire traverses the fascial plane in response to the user controlling the wire control mechanism and based at least in part on stiffness and flexibility characteristics of the feeler wire;
   wherein the feeler wire has a degree of stiffness that ensures that the feeler wire maintains an elongated shape when the feeler wire is traveling within the fascial plane, the feeler wire having a degree of flexibility that ensures that the elongated shape of the feeler wire temporarily deforms if the distal portion of the feeler wire contacts tissue outside of the fascial plane, wherein the temporary deformation of the elongated shape of the feeler wire is observable by an ultrasound machine thereby indicating location of the feeler wire within the fascial plane.

2. The medical device of claim 1, wherein the needle has a gauge that ranges between about 21 and 25.

3. The medical device of claim 1, wherein the feeler wire comprises Ninitol.

4. The medical device of claim 1, wherein the feeler wire has a hollow bore.

5. The medical device of claim 4, wherein the hollow bore of the feeler wire is adapted to allow a fluid to be passed through the hollow bore of the feeler wire and through the distal end of the feeler wire into the region of the patient's body.

6. The medical device of claim 4, further comprising:
   a catheter that extends over and about the feeler wire.

7. The medical device of claim 4, further comprising:
   a catheter that extends through and within the feeler wire.

8. The medical device of claim 1, wherein the second hollow bore extending from the proximal end of the needle to the distal end of the needle is generally parallel to the first hollow bore.

9. The medical device of claim 8, wherein the second hollow bore of the needle is adapted to allow a fluid to be passed through the second hollow bore of the needle and to be injected into the region of the patient's body through the distal end of the needle.

10. The medical device of claim 8, wherein the needle has a gauge that ranges between about 21 and 25.

11. The medical device of claim 8, wherein the feeler wire comprises Nitinol.

12. The medical device of claim 8, further comprising:
    a catheter disposed within the second hollow bore, wherein the second hollow bore of the needle is adapted to allow the catheter to extend through the second hollow bore of the needle and through the distal end of the needle into the region of the patient's body.

13. A medical device for use in a nerve block procedure to dispense a numbing agent into a fascial plane of a patient's body, the medical device comprising:
- a needle having a proximal end, a distal end, and at least a first hollow bore extending from the proximal end to the distal end, and at least a second hollow bore extending from the proximal end to the distal end, wherein the first hollow bore and the second hollow bore run in a parallel orientation and form the distal end of the needle by coming together in a single sharpened bevel to allow for permeation of the patient's body to reach the fascial plane;
- a wire control mechanism; and
- a feeler wire extending through the first hollow bore of the needle, the feeler wire comprising an echogenic material that is reflective to ultrasound energy, the feeler wire having a proximal end and a distal end and, the proximal end of the feeler wire being mechanically coupled to the wire control mechanism, wherein the wire control mechanism is configured to be controlled by a user to move the feeler wire from a non-deployed state to a deployed state, and vice versa, wherein when the distal end of the needle is disposed inside of the patient's body and the user controls the wire control mechanism to cause the feeler wire to move from the non-deployed state to the deployed state, a distal portion of the feeler wire that includes the distal end of the feeler wire extends out of the distal end of the needle into the patient's body and moves within a region of the fascial plane of the patient's body, wherein the feeler wire traverses the fascial plane in response to the user controlling the wire control mechanism and based at least in part on stiffness and flexibility characteristics of the feeler wire;
- wherein the feeler wire has a degree of stiffness that ensures that the feeler wire maintains an elongated shape when the feeler wire is moving within the fascial plane, the feeler wire having a degree of flexibility that ensures that the elongated shape of the feeler wire temporarily deforms if the distal portion of the feeler wire contacts tissue outside of the fascial plane, wherein the temporary deformation of the elongated shape of the feeler wire is observable by an ultrasound machine thereby indicating location of the feeler wire within the fascial plane.

14. The medical device of claim 13, wherein the second hollow bore of the needle is adapted to allow a fluid to be passed through the second hollow bore of the needle and through the distal end of the needle into the region of the patient's body.

15. The medical device of claim 13, further comprising a catheter disposed within the second hollow bore, wherein the second hollow bore of the needle is adapted to allow the catheter to extend through the second hollow bore of the needle and through the distal end of the needle into the region of the patient's body.

16. A method for locating a fascial plane when performing a nerve block procedure, the method comprising:
- inserting a distal end of a needle into a region of a patient's body, the needle having a proximal end, a first hollow bore extending from the proximal end to the distal end, and a second hollow bore extending from the proximal end to the distal end, wherein the distal end of the needle is formed by the first hollow bore and the second hollow bore coming together in a sharpened bevel to allow for permeation of the patient's body for the needle to reach the fascial plane;
- using a wire control mechanism to control movement of a feeler wire that extends through the first hollow bore of the needle, the feeler wire having a proximal end and a distal end and comprising an echogenic material that is reflective to ultrasound energy, the proximal end of the feeler wire being mechanically coupled to the wire control mechanism, wherein the feeler wire is controllable via the wire control mechanism to move the feeler wire from a non-deployed state to a deployed state, and vice versa, wherein when the distal end of the needle is disposed inside of the region of the patient's body and the feeler wire is moved from the non-deployed state to the deployed state, a distal portion of the feeler wire that includes the distal end of the feeler wire extends out of the distal end of the needle into the patient's body and moves within the region of the fascial plane of the patient's body; and
- with an ultrasound machine, providing a user with feedback to determine whether the distal portion of the feeler wire is within the fascial plane based at least in part on a shape of the distal portion of the feeler wire to allow the user to re-route the wire.

17. The method of claim 16, wherein the feeler wire has a degree of stiffness that ensures that the feeler wire maintains an elongated shape when the feeler wire is moving within the fascial plane, the feeler wire having a degree of flexibility that ensures that the elongated shape of the feeler wire temporarily deforms if the distal portion of the feeler wire contacts tissue outside of the fascial plane, wherein the temporary deformation of the elongated shape is observable by the ultrasound machine.

18. The method of claim 16, wherein the feeler wire has a hollow bore to allow a fluid to be passed through the hollow bore of the feeler wire and to be injected into the region of the patient's body through the distal end of the feeler wire, the method further comprising:
- if a determination is made that the distal portion of the feeler wire is within the fascial plane, injecting fluid through the hollow bore of the feeler wire and through the distal end of the feeler wire into the region of the patient's body.

19. The method of claim 16, wherein the second hollow bore of the needle is adapted to allow a fluid to be passed through the second hollow bore of the needle and to be injected into the region of the patient's body through the distal end of the needle, the method further comprising:
- if a determination is made that the distal portion of the feeler wire is within the fascial plane, injecting fluid through the second hollow bore of the needle and through the distal end of the needle into the region of the patient's body.

20. The method of claim 16, further comprising:
- if a determination is made that the distal portion of the feeler wire is not within the fascial plane, with the wire control mechanism, moving the feeler wire from the deployed state to the non-deployed state;
- repositioning the needle by inserting the distal end of the needle into a new region of a patient's body;
- with the wire control mechanism, moving the feeler wire from the non-deployed state to the deployed state to cause the distal portion of the feeler wire to extend out of the distal end of the needle into the patient's body and move within the new region of the patient's body; and with the ultrasound machine, determining whether the distal portion of the feeler wire is within the fascial plane based at least on the shape of the distal portion of the feeler wire.

* * * * *